US010448670B2

(12) United States Patent
Talon et al.

(10) Patent No.: US 10,448,670 B2
(45) Date of Patent: Oct. 22, 2019

(54) AEROSOL GENERATING SYSTEM WITH CONSUMPTION MONITORING AND FEEDBACK (71) Applicant: Philip Morris Products S.A., Neuchatel (CH)

(72) Inventors: Pascal Talon, Thonon-les-Bains (FR); Dionisius Florack, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 996 days.

(21) Appl. No.: 14/363,030

(22) PCT Filed: Dec. 28, 2012

(86) PCT No.: PCT/EP2012/077066
§ 371 (c)(1),
(2) Date: Jun. 5, 2014

(87) PCT Pub. No.: WO2013/098398
PCT Pub. Date: Jul. 4, 2013

(65) Prior Publication Data
US 2014/0345633 A1 Nov. 27, 2014

(30) Foreign Application Priority Data

Dec. 30, 2011 (EP) .................................... 11196227
Dec. 30, 2011 (EP) .................................... 11196240
Apr. 2, 2012 (EP) .................................... 12162894

(51) Int. Cl.
*A24F 47/00* (2006.01)
*A61M 15/06* (2006.01)
*A61M 11/04* (2006.01)
*A61M 16/16* (2006.01)
*G01F 15/06* (2006.01)
*G01N 33/00* (2006.01)
*A61M 15/00* (2006.01)
*A61M 16/00* (2006.01)

(52) U.S. Cl.
CPC ......... *A24F 47/008* (2013.01); *A61M 11/042* (2014.02); *A61M 15/008* (2014.02); *A61M 15/06* (2013.01); *A61M 16/024* (2017.08); *A61M 16/161* (2014.02); *G01F 15/06* (2013.01); *G01N 33/0004* (2013.01); *A61M 16/0051* (2013.01); *A61M 2016/0024* (2013.01); *A61M 2016/0033* (2013.01); *A61M 2205/3368* (2013.01); *A61M 2205/3375* (2013.01); *A61M 2205/3584* (2013.01); *A61M 2205/3592* (2013.01); *A61M 2205/502* (2013.01); *A61M 2205/52* (2013.01)

(58) Field of Classification Search
CPC .................. G01F 15/06; A61M 15/06; A61M 2205/3584; A61M 2205/52; A61M 2205/3592; A24F 47/008
See application file for complete search history.

(56) References Cited

U.S. PATENT DOCUMENTS

| 4,947,874 | A | 8/1990 | Brooks et al. |
| 5,269,327 | A | 12/1993 | Counts et al. |
| 5,505,214 | A | 4/1996 | Collins et al. |
| 5,613,504 | A | 3/1997 | Collins et al. |
| 5,692,291 | A | 12/1997 | Deevi et al. |
| 5,730,158 | A | 3/1998 | Collins et al. |
| 5,865,185 | A | 2/1999 | Collins et al. |
| 6,196,219 | B1 * | 3/2001 | Hess ................ A61M 15/0085 128/200.21 |
| 7,530,352 | B2 | 5/2009 | Childers et al. |
| 2004/0089314 | A1 | 5/2004 | Felter et al. |
| 2004/0129280 | A1 * | 7/2004 | Woodson ............. A24B 15/282 131/194 |
| 2004/0200488 | A1 | 10/2004 | Felter et al. |
| 2008/0257367 | A1 | 10/2008 | Paterno et al. |
| 2010/0163063 | A1 | 7/2010 | Fernando et al. |

(Continued)

FOREIGN PATENT DOCUMENTS

| CN | 101820781 A | 9/2010 |
| EA | 015651 B1 | 10/2011 |
| EP | 1 989 946 A1 | 11/2008 |

(Continued)

OTHER PUBLICATIONS

International Search Report dated Jul. 2, 2013 in PCT/EP12/077066 filed Dec. 28, 2012.
Written Opinion of the International Searching Authority dated Jul. 2, 2013 in PCT/EP12/077066 filed Dec. 28, 2012.
Extended European Search Report dated Jun. 1, 2012 in Patent Application No. 11196240.3.
Extended European Search Report dated Jun. 1, 2012 in Patent Application No. 11196227.0.
International Preliminary Report on Patentability and Written Opinion dated Jul. 10, 2014 in PCT/EP2012/077066.
English translation of Combined Chinese Office Action and Search Report dated Nov. 23, 2015 in Patent Application No. 201280062018.3.

(Continued)

*Primary Examiner* — Paul S Hyun
(74) *Attorney, Agent, or Firm* — Oblon, McClelland, Maier & Neustadt, L.L.P.

(57) ABSTRACT

An aerosol-generating system for oral or nasal delivery of a generated aerosol to a user is provided, including a heater element configured to heat an aerosol-forming substrate to generate an aerosol; a power source; a controller configured to control operation of the heater element, the controller being configured to detect a change in air flow past the heater element: a first data storage recording detected changes in airflow past the heater element and data relating to the operation of the heater element; a second data storage including a database relating changes in airflow and data relating to the operation of the heater element to the properties of the aerosol delivered to the user; and an indicator coupled to the second data storage configured to indicate to the user a property of the aerosol delivered to the user.

15 Claims, 4 Drawing Sheets

(56) References Cited

U.S. PATENT DOCUMENTS

| | | |
|---|---|---|
| 2010/0307518 A1 | 12/2010 | Wang |
| 2011/0265806 A1 | 11/2011 | Alarcon et al. |

FOREIGN PATENT DOCUMENTS

| | | |
|---|---|---|
| EP | 2 201 850 A1 | 6/2010 |
| JP | 3258657 B2 | 2/2002 |
| JP | 3904557 B2 | 4/2007 |
| JP | 2011-515093 A | 5/2011 |
| JP | 2013-524835 A | 6/2013 |
| KR | 10-2086488 B1 | 4/2001 |
| RU | 1837814 A3 | 8/1993 |
| WO | WO 94/18860 A1 | 9/1994 |
| WO | WO 02/098245 A1 | 12/2002 |
| WO | WO 2008/133091 A1 | 11/2008 |
| WO | WO 2009/115058 A1 | 9/2009 |
| WO | WO 2009/118085 A1 | 10/2009 |
| WO | WO 2010/091593 A1 | 8/2010 |
| WO | WO 2011/137453 A2 | 11/2011 |

OTHER PUBLICATIONS

Office Action dated Oct. 19, 2016 in Japanese Patent Application No. 2014-549492 (submitting English translation only).

Decision to Grant dated Jan. 11, 2017 in Russian Patent Application No. 2014131454 (with English translation).

Office Action dated Nov. 9, 2018 in Korean Patent Application No. 10-2014-7013157 (with English translation), 18 pages.

Korean Notice of Allowance with English translation dated May 17, 2019 in corresponding Korean Patent Application No. 2014-7013157, (6 pages).

\* cited by examiner

AEROSOL GENERATING SYSTEM WITH CONSUMPTION MONITORING AND FEEDBACK

CROSS REFERENCE TO RELATED APPLICATION

This application is a national phase application based on PCT/EP2012/077066, filed on Dec. 28, 2012.

This specification relates to aerosol-generating systems and in particular to systems including aerosol-generating devices for user inhalation, such as smoking devices. The specification relates to a device and method for monitoring the use of the device and providing to the user an indication of their aerosol consumption or their consumption of a particular constituent or constituents of the aerosol.

Conventional lit end cigarettes deliver smoke as a result of combustion of the tobacco and a wrapper which occurs at temperatures which may exceed 800 degrees Celsius during a puff. At these temperatures, the tobacco is thermally degraded by pyrolysis and combustion. The heat of combustion releases and generates various gaseous combustion products and distillates from the tobacco. The products are drawn through the cigarette and cool and condense to form a smoke containing the tastes and aromas associated with smoking. At combustion temperatures, not only tastes and aromas are generated but also a number of undesirable compounds.

Electrically heated smoking devices are known, which are essentially aerosol-generating devices, which operate at lower temperatures than conventional lit end cigarettes. An example of such an electrical smoking device is disclosed in WO2009/118085. WO2009/118085 discloses an electrical smoking device in which an aerosol-forming substrate is heated by a heater element to generate an aerosol. The temperature of the heater element is controlled to be within a particular range of temperatures in order to ensure that undesirable volatile compounds are not generated and released from the substrate while other, desired volatile compounds are released.

It is desirable to provide an aerosol-generating system which can provide the user with information about his or her consumption of aerosol or particular compounds in the aerosol, such as nicotine. This allows the use to better understand and regulate their consumption. It is also desirable to be able to collect system usage and aerosol consumption data for clinical studies and population level statistics.

In an aspect of the disclosure of this specification, there is provided an aerosol-generating system configured for oral or nasal delivery of a generated aerosol to a user, the system comprising:
 a heater element configured to heat an aerosol-forming substrate to generate an aerosol;
 a power source connected to the heater element;
 a controller connected to the heater element and to the power source, wherein the controller is configured to control operation of the heater element, the controller including or being connected to a means to detect a change in air flow past the heater element;
 first data storage means connected to the controller for recording detected changes in airflow past the heater element and data relating to the operation of the heater element; and
 second data storage means comprising a database relating changes in airflow and data relating to the operation of the heater element to the properties of the aerosol delivered to the user; and
 an indication means, such as a display, coupled to the second data storage means for indicating to the user a property of the aerosol delivered to the user.

The indication means may be a display that is able to display detailed information about the properties of the aerosol delivered to the user, such as amounts of particular compounds delivered to the user within a particular time period. However, the indication means may be more basic and may be an audible or visual alarm that is activated when consumption of a particular compound with a given time period exceeds a threshold level. The threshold level may be set by the user. As will be described, the indication means may be provided on an aerosol-generating device containing the heater element or may be provided on a secondary device to which data from an aerosol-generating device is sent.

As used herein aerosol "delivered" to a user means aerosol that is inhaled by the user during use. Inhaled as used herein, means drawn into the body through the mouth or nose and includes the situation where an aerosol is drawn into the user's lungs, and also the situation where an aerosol is only drawn into the user's mouth or nasal cavity before being expelled from the user's body.

The first data storage means may be configured to record detected changes in airflow or user puffs or inhalations. The first data storage means may record a count of user puffs or the time of each puff. The first data storage means may also be configured to record the temperature of the heater element and the power supplied during each puff. The first data storage means may record any available data from the controller, as desired.

The database may comprise data specific to a particular type of aerosol-forming substrate. The system may then comprise identifying means for identifying the aerosol-forming substrate received in the device. Identifying means may include an optical scanner for reading indicia on the aerosol-forming substrate or electronic circuitry configured to detect an electrical characteristic of the aerosol-forming substrate, such as a characteristic resistance. Alternatively, or in addition, the system may include a user interface configured to allow a consumer to input data identifying the aerosol-forming substrate received in the device.

The data relating to the operation of the aerosol-generating element may comprise the temperature of heater element or power supplied to the heater element. This information, together with airflow data, and optionally the identity of the substrate can be compared to stored data in the second data storage means to extract data describing properties of the aerosol delivered to the user. The properties of aerosol delivered to the user may comprise amounts of particular chemical compounds.

The database may include amounts of specific compounds delivered by the system under particular conditions, for particular substrates. The database may include formulas relating particular parameters of the operation of the aerosol-generating device, such as temperature and airflow, to amounts of specific compounds delivered by the system. The amounts and the formulas may be derived or extrapolated from experimental data.

The system may be an electrical smoking system. In the case of an electrical smoking system, the second data storage means may store information derived from smoking sessions using a standardized smoking machine under various smoking regimes and under controlled environment for smoking and controlled humidity for particular aerosol-forming substrates. This experimentally derived data can be used to extrapolate likely inhaled volume of mainstream smoke from the changes in airflow and operation of the heater. The smoking regimes using a standardized smoking machine may be, for example, the standard ISO regime or the Canadian intense regime.

In the case of a smoking system, the data stored in the second data storage means may include, but is not limited to amounts of the following compounds contained within the aerosol delivered: Acetaldehyde, Acetamide, Acetone, Acrolein, Acrylamide, Acrylonitrile, 4-Aminobiphenyl, 1-Aminonaphthalene, 2-Aminonaphthalene, Ammonia, Anabasine, o-Anisidine, Arsenic, A-$\alpha$-C (2-Amino-9H-pyrido[2,3-b]indole), Benz[a]anthracene, Benz[j]aceanthrylene, Benzene, Benzo[b]fluoranthene, Benzo[k]fluoranthene, Benzo[b]furan, Benzo[a]pyrene, Benzo[c]phenanthrene, Beryllium, 1,3-Butadiene, Cadmium, Caffeic acid, Carbon monoxide, Catechol, Chlorinated dioxins/furans, Chromium, Chrysene, Cobalt, Cresols (o-, m-, and p-cresol), Crotonaldehyde, Cyclopenta[c,d]pyrene, Dibenz[a,h]anthracene, Dibenzo[a,e]pyrene, Dibenzo[a,h]pyrene, Dibenzo[a,i]pyrene, Dibenzo[a,l]pyrene, 2,6-Dimethylaniline, Ethyl carbamate (urethane), Ethylbenzene, Ethylene oxide, Formaldehyde, Furan, Glu-P-1 (2-Amino-6-methyldipyrido[1,2-a:3',2'-d]imidazole), Glu-P-2 (2-Aminodipyrido[1,2-a:3',2'-d]imidazole), Hydrazine, Hydrogen cyanide, Indeno[1,2,3-cd]pyrene, IQ (2-Amino-3-methylimidazo[4,5-f]quinoline), Isoprene, Lead, MeA-$\alpha$-C (2-Amino-3-methyl)-9H-pyrido[2,3-b]indole), Mercury, Methyl ethyl ketone, 5-Methylchrysene, 4-(Methylnitrosamino)-1-(3-pyridyl)-1-butanone (NNK), Naphthalene, Nickel, Nicotine, Nitrobenzene, Nitromethane, 2-Nitropropane, N-Nitrosodiethanolamine (NDELA), N-Nitrosodiethylamine, N-Nitrosodimethylamine (NDMA), N-Nitrosomethylethylamine, N-Nitrosomorpholine (NMOR), N-Nitrosonornicotine (NNN), N-Nitrosopiperidine (NPIP), N-Nitrosopyrrolidine (NPYR), N-Nitrososarcosine (NSAR), Nornicotine, Phenol, PhIP (2-Amino-1-methyl-6-phenylimidazo[4,5-b]pyridine), Polonium-210, Propionaldehyde, Propylene oxide, Quinoline, Selenium, Styrene, o-Toluidine, Toluene, Trp-P-1 (3-Amino-1,4-dimethyl-5H-pyrido[4,3-b]indole), Trp-P-2 (1-Methyl-3-amino-5H-pyrido[4,3-b]indole), Uranium-235, Uranium-238, Vinyl acetate, or Vinyl chloride.

The system may comprise a single aerosol-generating device containing all of the components of the system. Alternatively, the system may comprise an aerosol-generating device and one or more secondary devices to which the aerosol-generating device may directly or indirectly couple or connect, with the one or more secondary devices comprising some of the components of the system. So, in the case of the system comprising a single device, the second data storage means or the display, or both the second data storage means and the display are contained within a single housing together with the heater element and the power source. The first data storage means and the second data storage means may be parts of a single physical memory. In alternative embodiments, the second data storage means or the display, or both the second data storage means and the display may be part of the one or more secondary devices. For example, a laptop computer may be part of the system and connectable to the aerosol-generating device. The laptop computer may contain the second data storage means and the display and may perform a comparison of the data from the first, data storage means with data in the second data storage means.

As used herein, aerosol-generating device means a device that interacts with an aerosol-forming substrate to generate an aerosol. An aerosol-generating device may comprise a power supply which may be an external power supply or an on-board power supply forming part of the aerosol-generating device.

The one or more secondary devices may be a charging device configured to replenish the power source in the aerosol-generating device. Alternatively, or in addition, the one or more secondary devices may comprise a laptop, desktop computer, mobile phone or other consumer electronic device. In one embodiment the second data storage means may comprise a remote server to which the aerosol-generating device or another secondary device can connect over a communications network. The user may be required to send the detected changes in airflow past the heater element and the data relating to the operation of the heater element (herein referred to as usage data) to the remote server in order to receive from the server the properties of the aerosol delivered to the user. This allows for central storage of usage data which can be used for population level statistics, may be used to improve system design and may be used in clinical studies.

Data may be transferred between different devices within the system by any suitable means. For example, a wired connection may used, such as a USB connection. Alternatively a wireless connection may be used. Data may also be transferred over a communications network, such as the Internet. In one embodiment, an aerosol-generating device may be configured to transfer data from the first data storage means to the second data storage means in a battery charging device every time the aerosol-generating device is recharged, through suitable data connections.

Any suitable type of memory may be used for the first and second data storage means, such as RAM or flash memory.

The identity or one of more characteristics of the aerosol-forming substrate may be provided before or after the recording of usage data. As described, the identity or one of more characteristics of the aerosol-forming substrate may be provided by a data input from the user of the system or may be provided as a result of an automated substrate detection process.

The system may be configured to provide an alert when a user is estimated to have been delivered a threshold amount of one or more compounds by the system within a predetermined time period. A plurality of thresholds may be set for different compounds and different time periods. The alert may be provided on an aerosol-generating device containing the heater element, or on one or more secondary devices. The alert may be a simple visual or audible signal or may be the presentation of more detailed information on a display screen. The alert may be provided to warn the user that their consumption of a particular compound has reached a desired limit or predetermined dose.

A user password or user name may be entered into a user interface in the system to ensure that recorded data is matched to previously recorded data from the same user. Alternatively, if the system includes one or more secondary devices in which the second data storage means is located, an assumption may be made that each aerosol-generating device is used by a unique user and a device identifier may be contained in usage data or in other data transferred from the aerosol-generating device.

In a second aspect of the disclosure of the specification, there is provided a method of providing aerosol delivery data to an end user of an electrically heated aerosol-generating device, the device comprising a heater element and a power supply for supplying power to the heater element, and means to detect a change in air flow past the heater element comprising:

recording detected changes in airflow past the heater element and data relating to the operation of the heater element; and extracting from a database, based on the detected changes in airflow and data relating to the operation of the heater element, properties of the aerosol delivered to the user; and indicating, for example displaying, the extracted properties of the aerosol delivered to the user.

The method may further comprise the step of detecting or providing at least one characteristic of the aerosol-forming substrate received in the device, wherein the step of extracting is also based on the at least one characteristic of the aerosol-forming substrate received in the device.

The extracted properties of the aerosol delivered to the user may comprise amounts of particular chemical compounds. The aerosol-generating device may be a smoking device.

In a third aspect of the disclosure of the specification, there is provided a computer program that when executed on a computer or other suitable processing device, carries out the method of second aspect or at least the steps of extracting and indicating.

In a fourth aspect of the disclosure of the specification, there is provided a computer readable storage medium carrying computer executable instructions that when executed on a computer or other suitable processing device, carry out the method of second aspect or at least the steps of extracting and indicating.

The computer executable instructions may be provided as an app or computer program for a personal computer or portable computing device such as a mobile phone or other processing device to which the aerosol-generating device could be connected. The app or computer program may downloadable by a user over a communications network, such as the Internet. The computer executable instructions may include the database or may include means to access the database stored on a remote device.

In a fifth aspect of the disclosure there is provided an aerosol-generating device configured for oral or nasal delivery of a generated aerosol to a user, the device comprising:

a heater element configured to heat an aerosol-forming substrate to generate an aerosol;

a power source connected to the heater element;

a controller connected to the heater element and to the power source, wherein the controller is configured to control operation of the heater element, the controller including or being connected to a means to detect a change in air flow past the heater element;

first data storage means connected to the controller for recording detected changes in airflow past the heater element and data relating to the operation of the heater element; and a data output means configured to allow data from the first data storage means to be output to an external device.

In a sixth aspect of the disclosure, there is provided a kit comprising: an electrically heated aerosol-generating device, the device comprising a heater element and a power supply for supplying power to the heater element, and means to detect a change in air flow past the heater element; and a computer readable storage medium carrying computer executable instructions or a code allowing for the download of computer executable instructions from a remote device, the computer executable instructions, when executed on a computer or other suitable processing device, carrying out the method of second aspect, or at least the steps of extracting and indicating.

In all aspects of the disclosure, the means to detect a change in airflow past the heater may be a dedicated flow sensor, such as a microphone or a thermocouple, connected to the controller. Alternatively, the controller may be configured to control power supplied to the heater element from the power source to maintain the heater element at a target temperature and may be configured to monitor changes in a temperature of the heater element or changes in the power supplied to the heater element to detect a change in air flow past the heater element.

The controller may judge, based on predetermined thresholds or based on a control loop, such as a Schmitt trigger, whether the detected changes in airflow are the result of a user puff. For example, in one embodiment the controller may be configured to monitor if a difference between the temperature of the heater element and the target temperature exceeds a threshold in order to detect a change in air flow past the heater element indicative of a user inhalation. The controller may be configured to monitor whether a difference between the temperature of the heater element and the target temperature exceeds a threshold for a predetermined time period or for a predetermined number of measurement cycles to detect a change in air flow past the heater element indicative of a user inhalation. This ensures that very short term fluctuations in temperature do not lead to false detection of a user inhalation.

In another embodiment the controller may be configured to monitor a difference between the power supplied to the heater element and an expected power level to detect a change in air flow past the heater element indicative of a user inhalation. Alternatively, or in addition, the controller may be configured to compare a rate of change of temperature or a rate of change of power supplied with a threshold level to detect a change in air flow past the heater element indicative of a user inhalation.

The controller may be configured to adjust the target temperature when a change in airflow past the heater is detected. Increased airflow brings more oxygen into contact with the substrate. This increases the likelihood of combustion of the substrate at a given temperature. Combustion of the substrate is undesirable. So the target temperature may be lowered when an increase in airflow is detected in order to reduce the likelihood of combustion of the substrate. Alternatively, or in addition, the controller may be configured to adjust the power supplied to the heater element when a change in airflow past the heater element is detected. Airflow past the heater element typically has a cooling effect on the heater element. The power to the heater element may be temporarily increased to compensate for this cooling.

In one embodiment, the controller may be configured to monitor the temperature of the heater element based on a measure of the electrical resistance of the heater element. This allows the temperature of the heater element to be detected without the need for additional sensing hardware.

The temperature of the heater element may be monitored at predetermined time intervals, such as every few milliseconds. This may be done continuously or only during periods when power is being supplied to the heater element.

The controller may be configured to reset, ready to detect the next user puff when the difference between the detected temperature and the target temperature is less than a threshold amount. The controller may be configured to require that the difference between the detected temperature and the target temperature is less than a threshold amount for a predetermined time or number of measurement cycles.

In some embodiments, the controller may be configured to compare a measure of power supplied to the heater element or energy supplied to the heater element from the power source to a threshold measure of power or energy to detect the presence of an aerosol-forming substrate close to the heater element or a material property of an aerosol-forming substrate close to the heater element.

The measure of power or energy can be any measure of power or energy, including average power over a predetermined time period or over a predetermined number of measurement cycles, a rate of change of power or energy or a cumulative measure of the power or energy supplied over a predetermined time period or over a predetermined number of measurement cycles.

In one embodiment, the measure of energy is normalised energy over a predetermined time period. In another embodiment, the measure of energy is a rate of decrease of normalised energy over a predetermined time period.

The amount of power or energy required to reach and maintain the heater element at a target temperature depends on the rate of heat loss from the heater element. This is strongly dependent on the environment surrounding the heater element. If a substrate is close to or contacts the heater element it will affect the rate of heat loss from the heater element compared to the situation in which there is no substrate close to the heater element. In one embodiment, the device is configured to receive an aerosol-forming substrate into contact with the heater element. The heater element then loses heat to the substrate by conduction. The device may be configured so that the substrate surrounds the heater element in use.

The controller may be configured to reduce to zero the supply of power to the heater element from the power source if the measure of power or energy is less than the threshold measure of power or energy. If the amount of energy needed to maintain the heater element temperature at a target temperature is less than expected, it may be because an aerosol-forming substrate is not present in the device or it may be that an unsuitable substrate, such as a previously used substrate, is in the device. A previously used substrate will typically have lower water content and lower aerosol former content than a new substrate and therefore draws less energy from the heater element. In either case it is usually desirable to stop the supply of power to the heater.

In all aspects of the disclosure, the power source may be any suitable power supply, such as a gas, chemical or electrical power supply. The power supply may be battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate or a Lithium-Polymer battery. Power may be supplied to the heater element as a pulsed signal. The amount of power delivered to the heater element may be adjusted by altering the duty cycle or the pulse width of the power signal.

The heater element may comprise a single heater element. Alternatively, the heater element may comprise more than one heater element. The heater element or heater elements may be arranged appropriately so as to most effectively heat the aerosol-forming substrate.

The heater element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum, gold, silver and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required. Ceramic and/or insulating materials may include, for example, aluminium oxide or zirconia oxide ($ZrO_2$). Alternatively, the electric heater may comprise an infra-red heater element, a photonic source, or an inductive heater element.

The heater element may take any suitable form. For example, the heater element may take the form of a heating blade. Alternatively, the heater element may take the form of a casing or substrate having different electro-conductive portions, or an electrically resistive metallic tube. Alternatively, one or more heating needles or rods that run through the centre of the aerosol-forming substrate may be as already described. Alternatively, the heater element may be a disk (end) heater or a combination of a disk heater with heating needles or rods. Other alternatives include a heating wire or filament, for example a Ni—Cr (Nickel-Chromium), platinum, tungsten or alloy wire or a heating plate. Optionally, the heater element may be deposited in or on a rigid carrier material. In one such embodiment, the heater element may be formed using a metal having a defined relationship between temperature and resistivity. In such an exemplary device, the metal may be formed as a track on a suitable insulating material, such as ceramic material, and then sandwiched in another insulating material, such as a glass. Heater elements formed in this manner may be used to both heat and monitor the temperature of the heaters during operation.

The heater element may heat the aerosol-forming substrate by means of conduction. The heater element may be at least partially in contact with the substrate, or the carrier on which the substrate is deposited. Alternatively, the heat from the heater element may be conducted to the substrate by means of a heat conductive element.

Alternatively, the heater element may transfer heat to the incoming ambient air that is drawn through the system during use, which in turn heats the aerosol-forming substrate by convection. The ambient air may be heated before passing through the aerosol-forming substrate.

In one embodiment, power is supplied to the heater element until the heater element reaches a temperature of between approximately 250° C. and 440° C. in order to produce an aerosol from the aerosol-forming substrate. Any suitable temperature sensor and control circuitry may be used in order to control heating of the heater element to reach the temperature of between approximately 250° C. and 440° C., including the use of one or more additional heater elements. This is in contrast to conventional cigarettes in which the combustion of tobacco and cigarette wrapper may reach 800° C.

The aerosol-forming substrate may be contained in a smoking article. During operation, the smoking article containing the aerosol-forming substrate may be completely contained within the aerosol-generating system. In that case, a user may puff on a mouthpiece of the aerosol-generating system. Alternatively, during operation the smoking article containing the aerosol-forming substrate may be partially contained within the aerosol-generating system. In that case, the user may puff directly on the smoking article.

The smoking article may be substantially cylindrical in shape. The smoking article may be substantially elongate. The smoking article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length. The aerosol-forming substrate may be received in the sliding receptacle of the aerosol-generating device such that the length of the aerosol-forming substrate is substantially parallel to the airflow direction in the aerosol-generating device.

The smoking article may have a total length between approximately 30 mm and approximately 100 mm. The smoking article may have an external diameter between approximately 5 mm and approximately 12 mm. The smoking article may comprise a filter plug. The filter plug may be located at the downstream end of the smoking article. The filter plug may be a cellulose acetate filter plug. The filter plug is approximately 7 mm in length in one embodiment, but may have a length of between approximately 5 mm to approximately 10 mm.

In one embodiment, the smoking article has a total length of approximately 45 mm. The smoking article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The smoking article may comprise an outer paper wrapper. Further, the smoking article may comprise a separation between the aerosol-forming substrate and the filter plug. The separation may be approximately 18 mm, but may be in the range of approximately 5 mm to approximately 25 mm.

As used herein, the term "aerosol-forming substrate" means a substrate capable of releasing volatile compounds that can form an aerosol. The volatile compounds may be released by heating or combusting the aerosol-forming substrate. The aerosol-forming substrate may comprise nicotine.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco comprises material formed by agglomerating particulate tobacco and may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise comminuting one or both of tobacco leaf lamina and tobacco leaf stems; alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

In a particularly preferred embodiment, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be used with other embodiments. For example, the aerosol-forming substrate may be a liquid aerosol-forming substrate. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating system or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid.

Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

The aerosol-generating system may comprise an air inlet. The aerosol-generating system may comprise an air outlet. The aerosol-generating system may comprise a condensation chamber for allowing the aerosol having the desired characteristics to form.

Embodiments will now be described in detail, by way of example only, with reference to the accompanying drawings, in which.

Figure 1:
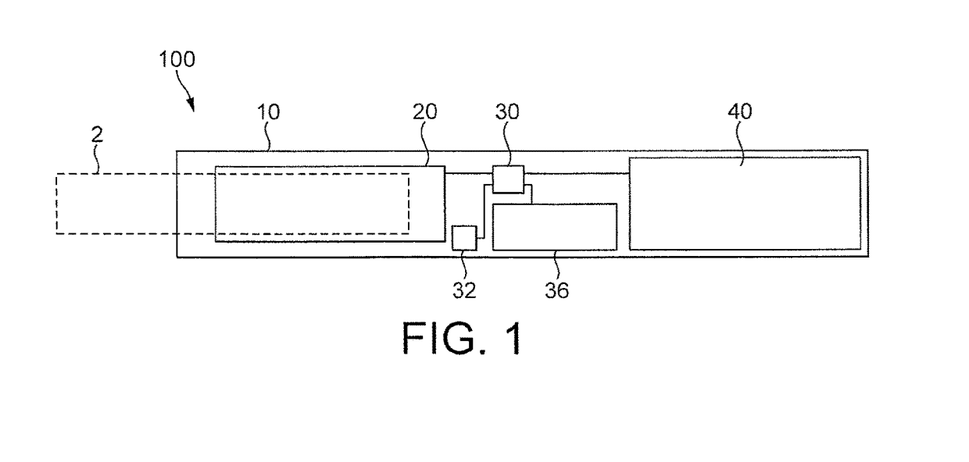
FIG. 1 is a schematic drawing showing the basic elements of an aerosol-generating device in accordance with one embodiment.

In FIG. 1, the inside of an embodiment of an aerosol-generating device 100 is shown in a simplified manner. Particularly, the elements of the aerosol-generating device 100 are not drawn to scale. Elements that are not relevant for the understanding of the embodiment discussed herein have been omitted to simplify FIG. 1.

The aerosol-generating device 100 comprises a housing 10 and an aerosol-forming substrate 2, for example a cigarette. The aerosol-forming substrate 2 is pushed inside the housing 10 to come into thermal proximity with the heater element 20. The aerosol-forming substrate 2 will release a range of volatile compounds at different temperatures. Some of the volatile compounds released from the aerosol-forming substrate 2 are only formed through the heating process. Each volatile compound will be released above a characteristic release temperature. By controlling the maximum operation temperature of the aerosol-generating device 100 to be below the release temperature of some of the volatile compounds, the release or formation of these smoke constituents can be avoided.

Additionally, the aerosol-generating device 100 includes an electrical energy supply 40, for example a rechargeable lithium ion battery, provided within the housing 10. The aerosol-generating device 100 further includes a controller 30 that is connected to the heater element 20, the electrical energy supply 40, an aerosol-forming substrate detector 32 and a user interface 36, for example a graphical display or a combination of LED indicator lights that convey information regarding device 100 to a user.

The aerosol-forming substrate detector 32 may detect the presence and identity of an aerosol-forming substrate 2 in thermal proximity with the heater element 20 and signals the presence of an aerosol-forming substrate 2 to the controller 30. The provision of a substrate detector is optional.

The controller 30 controls the user interface 36 to display system information, for example, battery power, temperature, status of aerosol-forming substrate 2, other messages or combinations thereof.

The controller 30 further controls the maximum operation temperature of the heater element 20. The temperature of the heater element can be detected by a dedicated temperature sensor. Alternatively, in another embodiment the temperature of the heater element is determined by monitoring its electrical resistivity. The electrical resistivity of a length of wire is dependent on its temperature. Resistivity ρ increases with increasing temperature. The actual resistivity ρ characteristic will vary depending on the exact composition of the alloy and the geometrical configuration of the heater element 20, and an empirically determined relationship can be used in the controller. Thus, knowledge of resistivity ρ at any given time can be used to deduce the actual operation temperature of the heater element 20.

The resistance of the heater element R=V/I; where V is the voltage across the heater element and I is the current passing through the heater element 20. The resistance R depends on the configuration of the heater element 20 as well as the temperature and is expressed by the following relationship:

$$R = \rho(T) * L/S \qquad \text{equation 1}$$

Where ρ (T) is the temperature dependent resistivity, L is length and S the cross-sectional area of the heater element 20. L and S are fixed for a given heater element 20 configuration and can be measured. Thus, for a given heater element design R is proportional to ρ (T).

The resistivity ρ(T) of the heater element can be expressed in polynomial form as follows:

$$\rho(T) \rho_o * (1 + \alpha_1 T + \alpha_2 T^2) \qquad \text{equation 2}$$

Where $\rho_o$ is the resistivity at a reference temperature $T_o$ and $\alpha_1$ and $\alpha_2$ are the polynominal coefficients.

Thus, knowing the length and cross-section of the heater element 20, it is possible to determine the resistance R, and therefore the resistivity $\rho$ at a given temperature by measuring the heater element voltage V and current I. The temperature can be obtained simply from a look-up table of the characteristic resistivity versus temperature relationship for the heater element being used or by evaluating the polynomial of equation (2) above. In one embodiment, the process may be simplified by representing the resistivity $\rho$ versus temperature curve in one or more, preferably two, linear approximations in the temperature range applicable to tobacco. This simplifies evaluation of temperature which is desirable in a controller 30 having limited computational resources.

Figure 2:
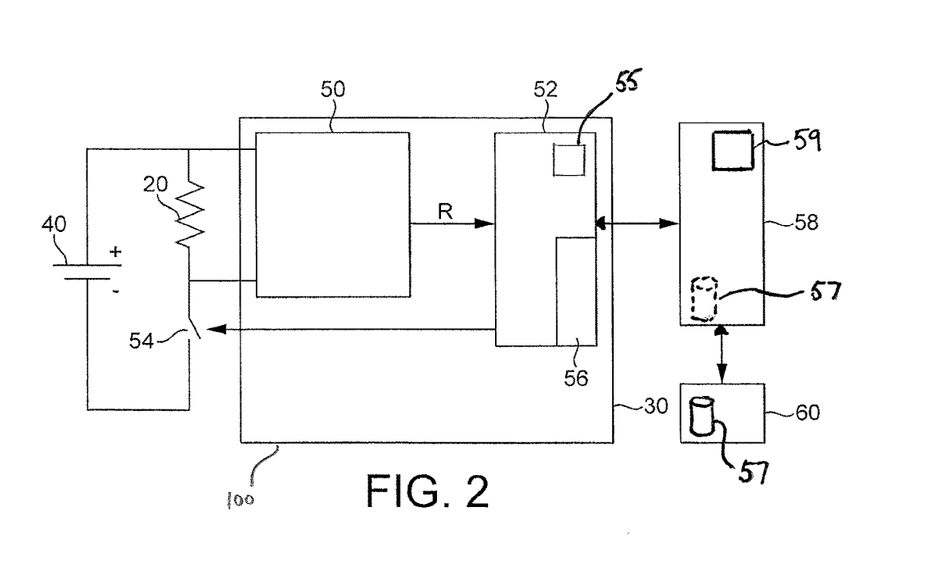
FIG. 2 is a schematic diagram illustrating the control elements of one embodiment.

FIG. 2 is a block diagram illustrating the control elements of a system including the device of FIG. 1 together with other system components. The system includes aerosol-generating device 100, secondary device 58 and optionally one or more remote devices 60. The aerosol-generating device 100 is as illustrated in FIG. 1, but only the control elements of the aerosol-generating device are shown in FIG. 2. As will be described, the secondary device 58 and one or more remote devices 60 operate to compare usage data from the aerosol-generating device with experimental usage data held within a database 57 that relates aerosol-generating device usage to the properties of the aerosol delivered to the user. The properties of the aerosol delivered to the user can then be displayed on a display 59 on the secondary device 58, or on a display on the aerosol-generating device or on an external device 60.

Referring to FIG. 2, the controller 30 includes a measurement unit 50 and a control unit 52. The measurement unit is configured to determine the resistance R of the heater element 20. The measurement unit 50 passes resistance measurements to the control unit 52. The control unit 52 then controls the provision of power from the battery 40 to the heater element 20 by toggling switch 54. The controller may comprise a microprocessor as well as separate electronic control circuitry. In one embodiment, the microprocessor may include standard functionality such as an internal clock in addition to other functionality.

In a preparation of the controlling of the temperature, a value for the target operation temperature of the aerosol-generating device 100 is selected. The selection is based on the release temperatures of the volatile compounds that should and should not be released. This predetermined value is then stored in the control unit 52. The control unit 52 includes a non-volatile memory 56.

The controller 30 controls the heating of the heater element 20 by controlling the supply electrical energy from the battery to the heater element 20. The controller 30 only allows for the supply of power to the heater element 20 if the aerosol-forming substrate detector 32 has detected an aerosol-forming substrate 20 and the user has activated the device. By the switching of switch 54, power is provided as a pulsed signal. The pulse width or duty cycle of the signal can be modulated by the control unit 52 to alter the amount of energy supplied to the heater element. In one embodiment, the duty cycle may be limited to 60-80%. This may provide additional safety and prevent a user from inadvertently raising the compensated temperature of the heater such that the substrate reaches a temperature above a combustion temperature.

In use, the controller 30 measures the resistivity $\rho$ of the heater element 20. The controller 30 then converts the resistivity of the heater element 20 into a value for the actual operation temperature of the heater element, by comparing the measured resistivity $\rho$ with the look-up table. This may be done within the measurement unit 50 or by the control unit 52. In the next step, the controller 30 compares the actual derived operation temperature with the target operation temperature. Alternatively, temperature values in the heating profile are pre-converted to resistance values so the controller regulates resistance instead of temperature, this avoids real-time computations to convert resistance to temperature during the smoking experience.

If the actual operation temperature is below the target operation temperature, then the control unit 52 supplies the heater element 20 with additional electrical energy in order to raise the actual operation temperature of the heater element 20. If the actual operation temperature is above the target operation temperature, the control unit 52 reduces the electrical energy supplied to the heater element 20 in order to lower the actual operation temperature back to the target operation temperature.

The control unit may implement any suitable control technique to regulate the temperature, such as a simple thermostatic feedback loop or a proportional, integral, derivative (PID) control technique.

The temperature of the heater element 20 is not only affected by the power being supplied to it. Airflow past the heater element 20 cools the heater element, reducing its temperature. This cooling effect can be exploited to detect changes in air flow through the device. The temperature of the heater element, and also its electrical resistance, will drop when air flow increases before the control unit 52 brings the heater element back to the target temperature.

Figure 3:
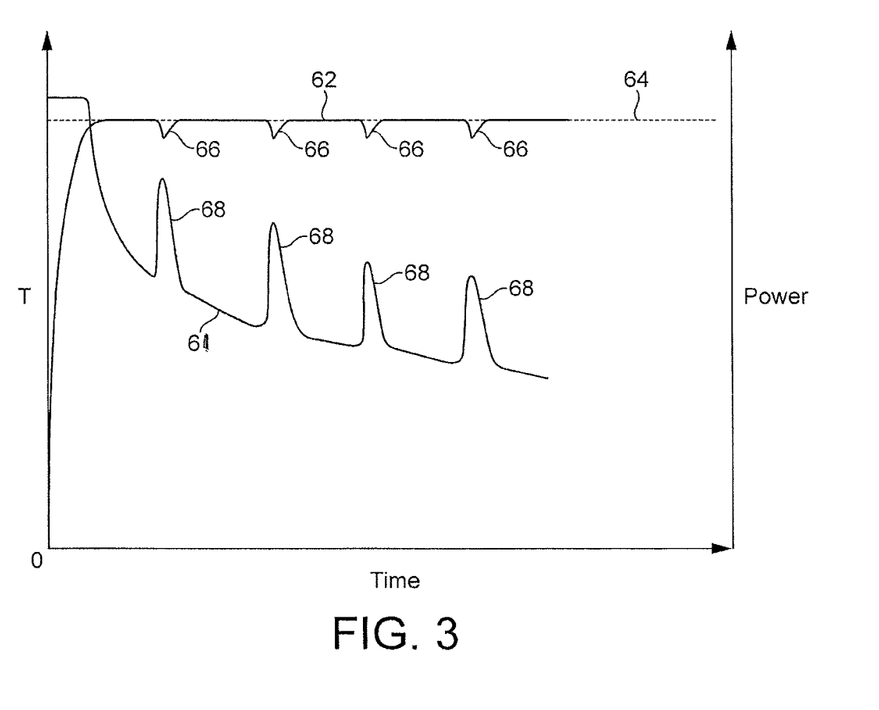
FIG. 3 is a graph illustrating changes in heater temperature and supplied power during user puffs in accordance with another embodiment.

FIG. 3 shows a typical evolution of heater element temperature and applied power during use of an aerosol-generating device of the type shown in FIG. 1. The level of supplied power is shown as line 61 and the temperature of the heater element as line 62. The target temperature is shown as dotted line 64.

An initial period of high power is required at the start of use in order to bring the heater element up to the target temperature as quickly as possible. Once the target temperature has been reached the applied power drops to the level required to maintain the heater element at the target temperature. However, when a user puffs on the substrate 2, air is drawn past the heater element and cools it below the target temperature. This is shown as feature 66 in FIG. 3. In order to return the heater element 20 to the target temperature there is a corresponding spike in the applied power, shown as feature 68 in FIG. 3. This pattern is repeated throughout the use of the device, in this example a smoking session, in which four puffs are taken.

Figure 4:
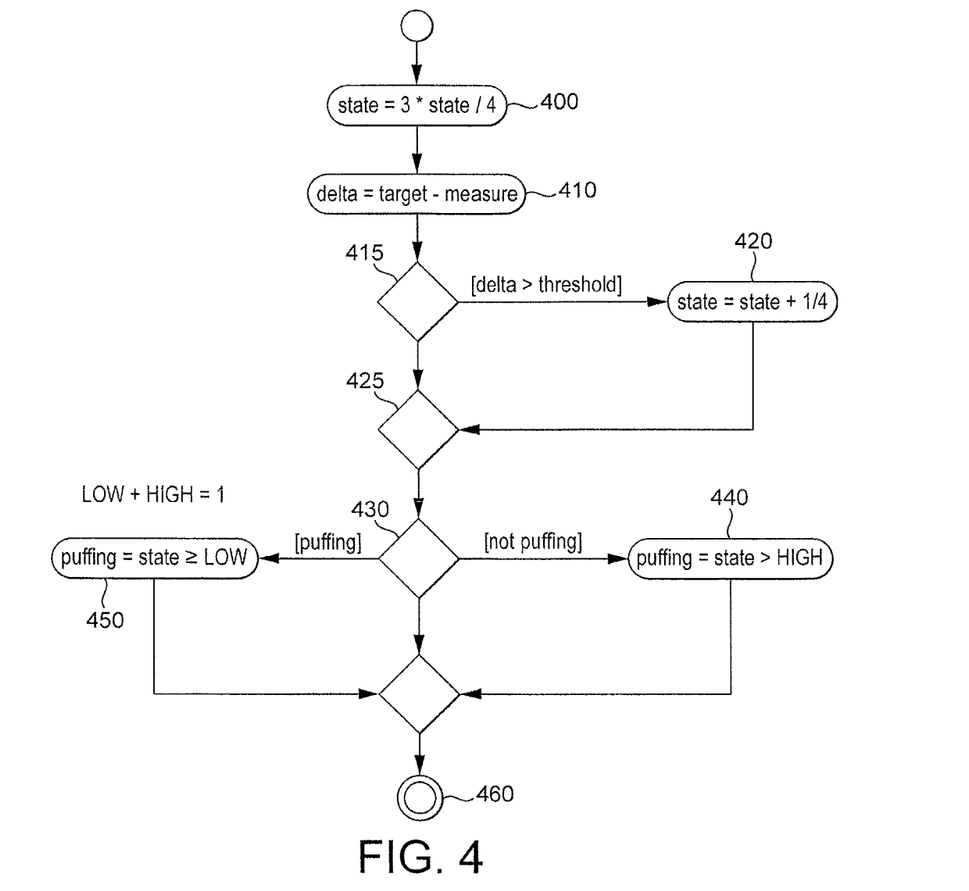
FIG. 4 illustrates a control sequence for determining if a user puff is taking place in accordance with an yet another embodiment.

By detecting temporary changes in temperature or power, or in the rate of change of temperature or power, user puffs or other airflow events can be detected. FIG. 4 illustrates an example of a control process, using a Schmitt trigger debounce approach, which can be used within control unit 52 to determine when a puff is taking place. The process in FIG. 4 is based on detecting changes in heater element temperature. In step 400 an arbitrary state variable, which is initially set as 0, is modified to three quarters of its original value. In step 410 a delta value is determined that is the difference between a measured temperature of the heater element and the target temperature. Steps 400 and 410 can be performed in reverse order or in parallel. In step 415 the delta value is compared with a delta threshold value. If the delta value is greater than the delta threshold then the state variable is increased by one quarter before passing to step 425. This is shown as step 420. If the delta value is less that the threshold the state variable is unchanged and the process moves to step 425. The state variable is then compared with a state threshold. The value of the state threshold used is different depending on whether the device is determined at that time to be in a puffing or not-puffing state. In step 430 the control unit determines whether the device is in a puffing or not-puffing state. Initially, i.e. in a first control cycle, the device is assumed to be in a not-puffing state.

If the device is in a not-puffing state the state variable is compared to a HIGH state threshold in step 440. If the state variable is higher than the HIGH state threshold then the device is determined to be in a puffing state. If not, it is determined to remain in a not-puffing state. In both cases, the process then passes to step 460 and then returns to 400.

If the device is in a puffing state the state variable is compared to a LOW state threshold in step 450. If the state variable is lower than the LOW state threshold then the device is determined to be in a not-puffing state. If not, it is determined to remain in a puffing state. In both cases, the process then passes to step 460 and then returns step to 400.

The value of the HIGH and LOW threshold values directly influence the number of cycles through the process are required to transition between not-puffing and puffing states, and vice versa. In this way very short term fluctuations in temperature and noise in the system, which are not the result of a user puff, can be prevented from being detected as a puff. Short fluctuations are effectively filtered out. However, the number of cycles required is desirably chosen so that the puff detection transition can take place before the device compensates for the drop in temperature by increasing the power delivered to the heater element. Alternatively the controller could suspend the compensation process while making the decision of whether a puff is taken or not. In one example LOW=0.06 and HIGH=0.94, which means that the system would need to go through at least 10 iterations when the delta value was greater than the delta threshold to go from not puffing to puffing.

The system illustrated in FIG. 4 can be used to provide a puff count and, if the controller includes a clock, an indication of the time at which each puff takes place. The puffing and not-puffing states can also be used to dynamically control the target temperature. Increased airflow brings more oxygen into contact with the substrate. This increases the likelihood of combustion of the substrate at a given temperature. Combustion of the substrate is undesirable. So the target temperature may be lowered when a puffing state is determined in order to reduce the likelihood of combustion of the substrate. The target temperature can then be returned to its original value when a not-puffing state is determined.

The process shown in FIG. 4 is just one example of a puff detection process. For example, similar processes to that illustrate in FIG. 4 could be carried out using applied power as a measure or using rate of change of temperature or rate of change of applied power. It is also possible to use a process similar to that shown in FIG. 4, but using only a single state threshold instead of different HIGH and LOW thresholds.

Figure 5:
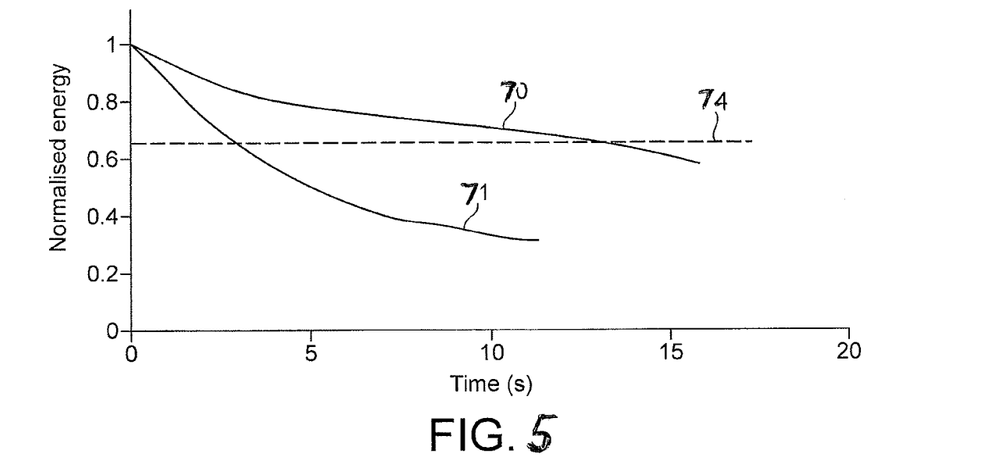
FIG. 5 is a graph illustrating the different the normalised energy required to be supplied to a heater element to maintain the temperature at a target level for new, old and no substrate next to the heater element.

The system can also automatically detect if an expected substrate is present or not. The amount of energy required to reach the target temperature and maintain the heater element at the target temperature depends on the presence or absence of a substrate material 2 close to the heater element 20, and on the properties of the substrate. FIG. 5 shows the evolution of normalised energy supplied to the heater element as a function of time. Curve 70 is the normalised energy when a new substrate is in the device and curve 72 is the normalised energy when no substrate is in the device. The normalised energy is the energy supplied during a fixed time interval normalised against an initial energy measurement. A normalised measure of energy minimises the influence of environmental conditions such as ambient temperature, airflow and humidity.

It can be seen that in both cases the power delivered to heater element monotonically decreases with time following an initial high power period to bring the heater element up to the target temperature. However, FIG. 5 shows that at T=10 seconds the amount of energy supplied with a new substrate in the device is about twice the amount of energy supplied when no substrate is present in the device. The difference in energy supplied between a new and a previously heated substrate is smaller but still detectable. In one embodiment, the difference in the normalized energy may be measured at T=5 seconds and accurately determine if a substrate is present or not.

The controller is able to calculate the normalised energy supplied to the heater element up to a predetermined time, and from that is able to determine if an expected or proper substrate is in the device.

Figure 6:
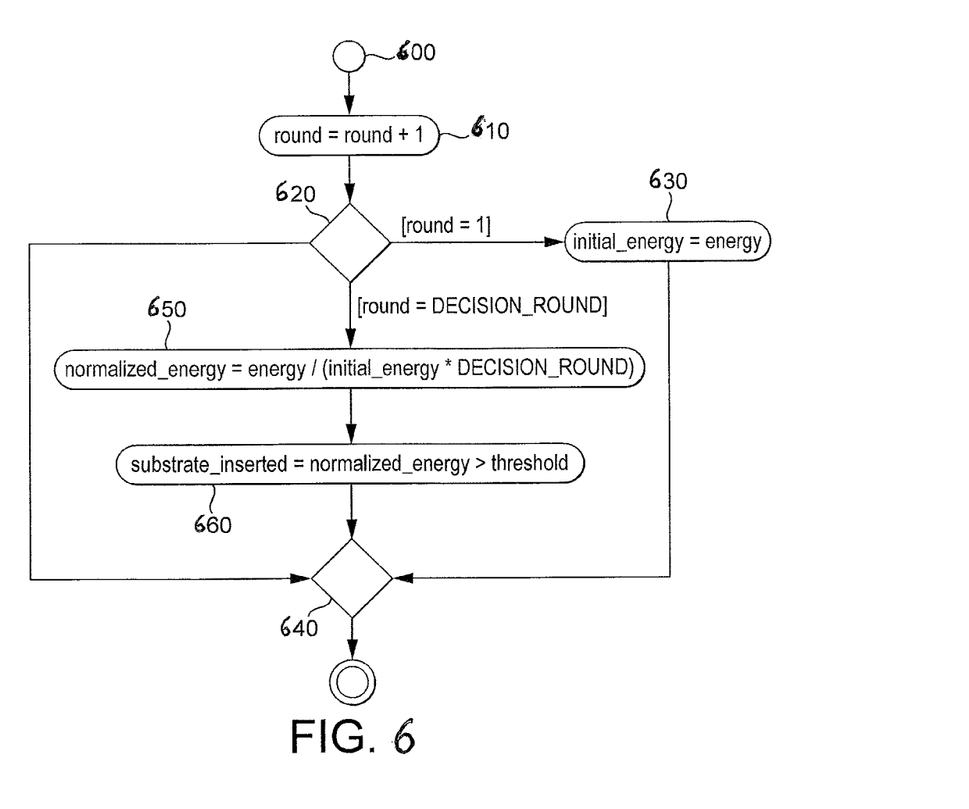
FIG. 6 illustrates a control sequence for determining if an appropriate substrate is in the device.

FIG. 6 illustrates an example of a control process that can be carried out by the control unit 52 to determine if a substrate is in the device or not. The process is a loop process and starts at step 600. In step 610 the round number is incremented. At the start of the process the round number is set to zero. Each time the control loop is passed through, the round number is incremented in step 610. At step 620 the process branches depending on the value of the round number. In the initial loop, when the round number equals one, the process passes to step 630. At step 630 the initial energy, i.e. the energy supplied to the heater so far, is set as the energy. This initial energy is used to normalise subsequent energy measurements. The process then passes to step 640 and back to step 610. Subsequent rounds pass directly from step 620 to step 640 until a decision round is reached. Each round may be carried out at a fixed time interval, for example every two seconds. The decision round corresponds to the time at which the controller is configured to compare the normalised energy with an expected or threshold value to determine if a substrate is present or not. The threshold value of normalised energy is illustrated by dotted line 74 in FIG. 3. In this example the decision round is round five, and occurs 10 seconds after the device is switched on. In the decision round, the process passes from step 620 to step 650. In step 650 the normalised energy is calculated as the energy supplied since the device was switched on divided by the product of the initial energy and the decision round number (in this example five). The calculated normalised energy is then compared to a threshold value in step 660. If the normalised energy exceeds the threshold value then the control unit determines that an appropriate substrate is present and the device can continue to be used. If the normalised energy does not exceed the threshold, the control unit determines that no substrate (or an inappropriate substrate) is present and the control unit then prevents the supply of power to the heater element by holding switch 54 open.

The process illustrated in FIG. 6 is just one example of a process for determining if an appropriate substrate is present in an aerosol-generating device. Other measures of power or energy supplied to the heater element may be used and normalised or non-normalised data may be used. The time at which the determination is made is also a matter of choice. The advantage of an early determination in order to take early action if necessary must be balanced against the need to obtain a reliable result.

The measure of power or energy can be compared to a plurality of thresholds. This may be useful to distinguish between different types of substrate or between an inappropriate substrate and the absence of any substrate.

As well as being useful for dynamic control of the aerosol-generating device, the puff detection data and substrate detection data determined by the controller 30 may be useful for analysis purposes. In particular, the puff detection data together with data relating to the temperature of the heater element and/or the power supplied to the heater element (collectively referred to as usage data herein) can be compared with stored, experimentally derived data relating usage data to properties of the aerosol delivered by the device under different usage scenarios. The properties of the aerosol delivered can be provided to the user as feedback on his or her consumption of aerosol and of key constituents of the aerosol. The properties of the aerosol can also be collected over time and from several different users to provide a population level data set that can be subsequently analysed.

The stored, experimentally derived data relating usage data to properties of the aerosol delivered by the device under different usage scenarios can be contained in a database and can be held on the aerosol-generating device or on a secondary device to which the aerosol-generating device can be connected. The secondary device may be any processing device, such as a laptop computer or a mobile phone. In one embodiment the secondary device is a charging device for recharging the battery in the aerosol-generating device.

It will be apparent to one of ordinary skill that, to the extent that additional environment data is required to accurately compare actual user data and the experimentally derived data, the control unit 52 may include additional sensing functionality to provide such environmental data. For example, the control unit 52 may include a humidity sensor 55 and humidity data may be included as part of the data eventually provided to the external device 58. Alternatively, or in addition, sensor 55 may be an ambient temperature sensor.

The usage of the device may also be analysed by an external device 58, 60 to determine which experimentally derived data most closely matches the usage behaviour, for example in terms of length and frequency of inhalation and number of inhalations. The experimentally derived data with the most closely matching usage behaviour may then be used as the basis for further analysis and display.

FIG. 2 illustrates connection of the controller 30 to an external secondary device 58 including a display 59. The puff count and time data can be exported to the external device 58 together with other captured usage data and may be further relayed from the secondary device 58 to other external processing or data storage devices 60. The aerosol-generating device may include any suitable data output means. For example the aerosol-generating device may include a wireless radio connected to the controller 30 or memory 56, or a universal serial bus (USB) socket connected to the controller 30 or memory 56.

Alternatively, the aerosol-generating device may be configured to transfer data from the memory to an external memory in a battery charging device every time the aerosol-generating device is recharged through suitable data connections. The battery charging device can provide a larger memory for longer term storage of the puff data and can be subsequently connected to a suitable data processing device or to a communications network. In addition, data as well as instructions for controller 30 may be uploaded, for example, to control unit 52 when controller 30 is connected to the external device 58.

Additional data may also be collected during operation of aerosol-generating device 100 and transferred to the external device 58. Such data may include, for example, a serial number or other identifying information of the aerosol-generating device; the time at start of smoking session; the time of the end of smoking session; and information related to the reason for ending a smoking session.

In one embodiment, a serial number or other identifying information, or tracking information, associated with the aerosol-generating device 100 may be stored within controller 30. For example, such tracking information may be stored in memory 56. Because the aerosol-generating device 100 may be not always be connected to the same external device 58 for charging or data transfer purposes, this tracking information can be exported to external processing or data storage devices 60 and gathered to provide a more complete picture of the user's behaviour. A serial number or other identifying information allows the usage data from the device to be associated with previously stored usage data from the same device.

It will now be apparent to one of ordinary skill in the art that knowledge of the time of the operation of the aerosol-generating device, such as a start and stop of the smoking session, may also be captured using the methods and apparatuses described herein. For example, using the clock functionality of the controller 30 or the control unit 52, a start time of the smoking session may be captured and stored by controller 30. Similarly, a stop time may be recorded when the user or the aerosol-generating device 100 ends the session by stopping power to the heater element 20. The accuracy of such start and stop times may further be enhanced if a more accurate time is uploaded to the controller 30 by the external device 58 to correct any loss or inaccuracy. For example, during a connection of the controller 30 to the external device 58, device 58 may interrogate the internal clock function of the controller 30, compare the received time value with a clock provided within external device 58 or one or more of external processing or data storage devices 60, and provide an updated clock signal to controller 30.

The reason for terminating a smoking session or operation of the aerosol-generating device 100 may also be identified and captured. For example, control unit 52 may contain a look up table that includes various reasons for the end of the smoking session or operation. An exemplary listing of such reasons is provided here.

| Session code | Reason for session ending | Description of reason |
|---|---|---|
| 0 | (normal end) | End of session reached |
| 1 | (stop by user) | The user aborted the experience (by pushing power button to end session, by inserting aerosol-generating device into the external device 58, or via a remote control command |
| 2 | (heater broken) | Suspected heater damage in view of temperature measurements outside of a predetermined range during heating |
| 3 | (incorrect heating level) | Malfunction occurs where heater element temperature overshoots or undershoots a predetermined operating temperature outside of an acceptable tolerance range |

| Session code | Reason for session ending | Description of reason |
|---|---|---|
| 4 | (external heating) | Heater element temperature remains higher than the target even if the supplied power is reduced |

The above table provides a number of exemplary reasons why operation or a smoking session may be terminated. It will now be apparent to one of ordinary skill in the art, by using various indications provided by the measurement unit 50 and the control unit 52 provided in the controller 30, either alone or in combination with recorded indications in response to the controller 30 control of the heating of the heater element 20, controller 30 may assign session codes with a reason for ending the operation of aerosol-generating device 100 or a smoking session using such a device. Other reasons that may be determined from available data using the above described methods and apparatuses will now be apparent to one of ordinary skill in the art and may also be implemented using the methods and apparatuses described herein without deviating from the scope or spirit of this specification and the exemplary embodiments described herein.

The user's consumption of aerosol deliverables may be accurately approximated because the aerosol-generating device 100 described herein may accurately control the temperature of the heater element 20, and because data may be gathered by the controller 30, as well as the units 50 and 52 provided within the controller 30, and an accurate profile of the actual use of the device 100 during a session can be obtained.

In one exemplary embodiment, the usage data captured by the controller 30 can be compared to data determined during controlled sessions to even further enhance the understanding of the user use of the device 100. For example, by first collecting data using a smoking machine under controlled environmental conditions and measuring data such as the puff number, puffing volume, puff interval, and resistivity of heater element, a database 57 can be constructed that provides, for examples, levels of nicotine or other deliverables provided under the experimental conditions. Such experimental data can then be compared to data collected by the controller 30 during actual use and be used to determine, for example, information on how much of a deliverable the user has inhaled. In one embodiment, as illustrated in FIG. 2, such a database 57 containing experimental data may be stored in one or more of remote devices 60 and additional comparison and processing of the data may take place in one or more of devices 60. For example, remote devices 60 may be one or more servers operated by a manufacturer of aerosol-generating devices connected to and accessible from the Internet. Alternatively, database 57 may be located within external device 58, as illustrated in dotted line in FIG. 2.

The database 57 may comprise data for a plurality of different types of aerosol-forming substrate and for a plurality of different types of aerosol-generating device. An indication of the type of substrate and the type of device may be provided by the user either before a smoking session or after a smoking session and may be input into the aerosol-generating device or into one of the secondary devices. Alternatively an indication of the type of substrate and the type of device may be provided automatically by the aerosol-generating device as part of the usage data.

The data stored in the database 57 may include amounts of the following compounds contained within the aerosol delivered under particular operating conditions: Acetaldehyde, Acetamide, Acetone, Acrolein, Acrylamide, Acrylonitrile, 4-Aminobiphenyl, 1-Aminonaphthalene, 2-Aminonaphthalene, Ammonia, Anabasine, o-Anisidine, Arsenic, A-α-C (2-Amino-9H-pyrido[2,3-b]indole), Benz[a]anthracene, Benz[j]aceanthrylene, Benzene, Benzo[b]fluoranthene, Benzo[k]fluoranthene, Benzo[b]furan, Benzo[a]pyrene, Benzo[c]phenanthrene, Beryllium, 1,3-Butadiene, Cadmium, Caffeic acid, Carbon monoxide, Catechol, Chlorinated dioxins/furans, Chromium, Chrysene, Cobalt, Cresols (o-, m-, and p-cresol), Crotonaldehyde, Cyclopenta[c,d]pyrene, Dibenz[a,h]anthracene, Dibenzo[a,e]pyrene, Dibenzo[a,h]pyrene, Dibenzo[a,i]pyrene, Dibenzo[a,l]pyrene, 2,6-Dimethylaniline, Ethyl carbamate (urethane), Ethylbenzene, Ethylene oxide, Formaldehyde, Furan, Glu-P-1 (2-Amino-6-methyldipyrido[1,2-a:3',2'-d]imidazole), Glu-P-2 (2-Aminodipyrido[1,2-a:3',2'-d]imidazole), Hydrazine, Hydrogen cyanide, Indeno[1,2,3-cd]pyrene, IQ (2-Amino-3-methylimidazo[4,5-f]quinoline), Isoprene, Lead, MeA-α-C (2-Amino-3-methyl)-9H-pyrido[2,3-b]indole), Mercury, Methyl ethyl ketone, 5-Methylchrysene, 4-(Methylnitrosamino)-1-(3-pyridyl)-1-butanone (NNK), Naphthalene, Nickel, Nicotine, Nitrobenzene, Nitromethane, 2-Nitropropane, N-Nitrosodiethanolamine (NDELA), N-Nitrosodiethylamine, N-Nitrosodimethylamine (NDMA), N-Nitrosomethylethylamine, N-Nitrosomorpholine (NMOR), N-Nitrosonornicotine (NNN), N-Nitrosopiperidine (NPIP), N-Nitrosopyrrolidine (NPYR), N-Nitrososarcosine (NSAR), Nornicotine, Phenol, PhIP (2-Amino-1-methyl-6-phenylimidazo[4,5-b]pyridine), Polonium-210, Propionaldehyde, Propylene oxide, Quinoline, Selenium, Styrene, o-Toluidine, Toluene, Trp-P-1 (3-Amino-1,4-dimethyl-5H-pyrido[4,3-b]indole), Trp-P-2 (1-Methyl-3-amino-5H-pyrido[4,3-b]indole), Uranium-235, Uranium-238, Vinyl acetate, or Vinyl chloride.

The information about the properties of the aerosol delivered to the user may displayed on the aerosol-generating device 100 or may be displayed on the display 59 of a secondary device 58, such as a mobile phone or charging device, or on a remote, external device 60.

It will now be apparent to one of ordinary skill in the art, that using the methods and apparatuses discussed herein, nearly any desired information may be captured by such that comparison to experimental data is possible and various attributes associated with a user's operation of the aerosol-generating device 100 be accurately approximated.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. A method of providing aerosol delivery data to an end user of an electrically heated aerosol-generating device, the device comprising a heater element and a power supply configured to supply power to the heater element, and means to detect a change in air flow past the heater element, the method comprising:
   recording in a first database detected changes in air flow past the heater element and data relating to operation of the heater element;
   using the detected changes in airflow and data relating to the operation of the heater element from the first database to extract from a second database relating changes in air flow and data relating to the operation of the heater element to properties of an aerosol delivered to the user; and indicating, using an indication means coupled to the second database, the extracted properties of the aerosol delivered to the user.

2. The method according to claim 1, further comprising a step of detecting or providing at least one characteristic of an aerosol-forming substrate received in the device, wherein the step of extracting is also based on the at least one characteristic of the aerosol-forming substrate received in the device.

3. The method according to claim 1, wherein the extracted properties of the aerosol delivered to the user comprise amounts of particular chemical compounds.

4. A non-transitory computer readable storage medium having a computer program stored thereon that when executed on a computer or other suitable processing device, causes the computer or the suitable processing device to carry out the method of claim 1.

5. An aerosol-generating system configured for oral or nasal delivery of a generated aerosol to a user, the system comprising:
a heater element configured to heat an aerosol-forming substrate to generate an aerosol;
a power source connected to the heater element;
a controller connected to the heater element and to the power source, wherein the controller is configured to control operation of the heater element, the controller including or being connected to a means to detect a change in air flow past the heater element;
a first data storage means comprising a first database connected to the controller for recording detected changes in air flow past the heater element and data relating to the operation of the heater element;
a second data storage means comprising a second database relating changes in air flow and data relating to the operation of the heater element to properties of the aerosol delivered to the user; and
an indication means coupled to the second data storage means for indicating the properties of the aerosol delivered to the user,
wherein the aerosol-generating system is configured to use the detected changes in air flow past the heater element and the data relating to the operation of the heater element from the first database to extract the properties of the aerosol delivered to the user from the second database.

6. The aerosol-generating system according to claim 5, wherein the controller is further configured to control power supplied to the heater element from the power source to maintain the heater element at a target temperature, and is further configured to monitor changes in a temperature of the heater element or changes in the power supplied to the heater element.

7. The aerosol-generating system according to claim 5, wherein the second database comprises data specific to a particular type of aerosol-forming substrate.

8. The aerosol-generating system according to claim 7, further comprising identifying means for identifying the aerosol-forming substrate received in the system or a user interface configured to allow a consumer to input data identifying the aerosol-forming substrate received in the system.

9. The aerosol-generating system according to claim 5, wherein the data relating to the operation of the heater element comprises a temperature of the heater element or power supplied to the heater element.

10. The aerosol-generating system according to claim 5, comprising a housing, wherein the second data storage means or a display, or both the second data storage means and the display, are contained within the housing together with at least one of the heater element and the power source.

11. The aerosol-generating system according to claim 5, wherein the heater element, the power source, and the controller are components of an aerosol-generating device, and
further comprising one or more secondary devices to which the aerosol-generating device may be directly or indirectly coupled, wherein at least the second data storage means and a display are part of the one or more secondary devices.

12. The aerosol-generating system according to claim 11, wherein the secondary device is a charging device configured to replenish the power source in the aerosol-generating device.

13. The aerosol-generating system according to claim 5, wherein the properties of the aerosol delivered to the user comprise amounts of particular chemical compounds.

14. The aerosol-generating system according to claim 5, wherein the system is further configured to provide an alert when the user is estimated to have been delivered a threshold amount of a compound within a predetermined time period, and
wherein the system is further configured to set a plurality of threshold amounts for a plurality of different compounds.

15. The aerosol-generating system according to claim 5, wherein the system is an electrical smoking device.

* * * * *